US007588579B2

United States Patent
Mommaerts

(10) Patent No.: US 7,588,579 B2
(45) Date of Patent: Sep. 15, 2009

(54) APPARATUS FOR INTRAORAL DISTRACTION OSTEOTOMY TO WIDEN THE UPPER JAW

(75) Inventor: Maurice Yves Mommaerts, Sint Martens-Latem (BE)

(73) Assignee: Synthes USA, LLC, West Chester, PA (US)

( * ) Notice: Subject to any disclaimer, the term of this patent is extended or adjusted under 35 U.S.C. 154(b) by 107 days.

(21) Appl. No.: 11/070,862

(22) Filed: Mar. 2, 2005

(65) Prior Publication Data

US 2005/0203534 A1 Sep. 15, 2005

Related U.S. Application Data

(63) Continuation-in-part of application No. 10/193,695, filed on Jul. 11, 2002, now abandoned, which is a continuation of application No. PCT/EP01/00398, filed on Jan. 11, 2001.

(30) Foreign Application Priority Data

Jan. 11, 2000 (BE) .................................. 2000/0016

(51) Int. Cl.
*A61B 17/66* (2006.01)
(52) U.S. Cl. ..................... 606/105; 606/282; 606/90; 606/57
(58) Field of Classification Search ............. 606/90, 606/104; 433/7
See application file for complete search history.

(56) References Cited

U.S. PATENT DOCUMENTS

| 360,695 A | 4/1887 | Holmes |
| 597,582 A | 1/1898 | Knapp |
| 3,473,528 A | 10/1969 | Mishkin et al. |
| 4,144,643 A * | 3/1979 | Krygier .................. 433/7 |

(Continued)

FOREIGN PATENT DOCUMENTS

AT 192049 9/1957

(Continued)

OTHER PUBLICATIONS

"malleable". Merriam-Webster Online Dictionary [online], [retrieved on Nov. 9, 2006], Retrieved from the internet <URL: www.m-w.com.*

(Continued)

*Primary Examiner*—Eduardo C Robert
*Assistant Examiner*—Jerry Cumberledge
(74) *Attorney, Agent, or Firm*—Woodcock Washburn LLP

(57) ABSTRACT

A distraction device used to widen an upper jaw after cortical osteotomy and fixation of an adjustable bridging onto the bone of the palate with the goal to increase the distance between two mutually opposite halves of the jaw by means of gradual expansion. An orthopedic system that may be used intra-orally in a patient for the modification of the distance between the contralateral maxillary segments or halves in relation to each other. Two metal bone-plates may be fixed on the bony palatal shelves, the plate may include slotted extensions forming a receiving space into which disk-shaped wings of interchangeable distraction modules fit. The palatal plane concave female indent and the convex male wing pervert distraction module dislocation in case of oblique placement in the axial plane. In the frontal plane, the male wings are straight.

24 Claims, 5 Drawing Sheets

U.S. PATENT DOCUMENTS

| | | | |
|---|---|---|---|
| 4,308,863 A | 1/1982 | Fischer | |
| 4,445,513 A * | 5/1984 | Ulrich et al. | 606/61 |
| 4,848,368 A | 7/1989 | Kronner | |
| 5,564,920 A | 10/1996 | Klapper et al. | |
| 5,575,790 A * | 11/1996 | Chen et al. | 606/60 |
| 5,769,850 A * | 6/1998 | Chin | 606/53 |
| 5,885,290 A | 3/1999 | Guerrero et al. | |
| 5,902,304 A * | 5/1999 | Walker et al. | 606/71 |
| 5,993,448 A * | 11/1999 | Remmler | 606/53 |
| 6,206,882 B1 * | 3/2001 | Cohen | 606/69 |
| 6,267,589 B1 | 7/2001 | Farzin-Nia et al. | |
| 6,328,745 B1 * | 12/2001 | Ascherman | 606/86 |
| 2002/0031741 A1 | 3/2002 | Williams | |

FOREIGN PATENT DOCUMENTS

| | | |
|---|---|---|
| DE | 1 049 533 | 1/1959 |
| EP | 0846446 | 6/1998 |
| EP | 0706349 | 8/1999 |
| WO | 96/28110 | 9/1996 |
| WO | 96/29964 | 10/1996 |
| WO | 98/10708 | 3/1998 |

OTHER PUBLICATIONS

"thread". Merriam-Webster Online Dictionary [online], [retrieved on Nov. 9, 2006], Retrieved from the Internet <URL: www.m-w.com.*

English Abstract of WO 96/28110 dated Sep. 19, 1996.

English Abstract of WO 98/10708 dated Mar. 19, 1998.

Mommaerts, M.Y. "Transpalatal distraction as a method of maxillary expansion" *British Journal of Oral and Maxillofacial Surgery* (1999) 37, pp. 268-272.

* cited by examiner

APPARATUS FOR INTRAORAL DISTRACTION OSTEOTOMY TO WIDEN THE UPPER JAW This is a Continuation-in-part of U.S. patent application Ser. No. 10/193,695, filed Jul. 11, 2002 now abandoned, which application is a continuation of International patent application PCT/EP01/00398, filed Jan. 11, 2001.

BACKGROUND OF THE INVENTION

The present invention pertains to a distraction device used to widen an upper jaw (maxillae) after cortical osteotomy and fixation of an adjustable bridging onto the bone of the palate with the goal to increase the distance between the two mutually opposite halves of the jaw by means of gradual expansion.

In addition, the present invention relates to an improved orthopaedic system wherein the device is used intra-orally in a patient to achieve a change in transverse position of two upper jaw halves or segments in relation to each other.

The device is used in maxillofacial surgery, in particular in orthognathic surgery in patients with too narrow maxillae or upper jaw. It concerns a developmental disturbance, sometimes congenital as in cleft lip and palate, which can lead to a cross-bite, tooth crowding, hindered nasal breathing, a disturbed occlusion with the lower dental arch, and a psychosocial aesthetic problem. The aim of the invention is to restore the dental occlusion, to improve nasal breathing and to bring the face into normal proportions.

SUMMARY OF THE INVENTION

From one aspect, the invention provides a Distraction apparatus for expansion of an upper jaw bone after osteotomy by application of distraction forces directly to a bone of a palate with the aim to reconstruct the jaw by increasing a distance between two op-posing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, wherein the ends of the distractor module are disk-shaped or flat.

In one embodiment, the ends have a convex disk end edge. In a further development hereof, the end edge is circular.

In one embodiment, the disk has two opposite planes that are parallel to one another.

In one embodiment, the ends are widened with respect to an arm portion connection to the arm ends.

The disk-shaped ends may merge into the distraction module via a neck.

In one embodiment, the extension forms a receiving space for receipt of the disk-shaped ends of the distraction module.

The receiving space may have two opposite walls that face the main planes of the disk shaped ends and diverge from one another in a direction towards the distraction module.

The disk-shaped ends may merge into the distraction module via a neck, wherein the extension forms a receiving space for receipt of the disk-shaped ends of the distraction module, wherein the receiving space has an opening which is narrowed with respect to the receiving space and adapted to accommodate the neck.

From a further aspect, the abutment plates may comprise base plates which are provided with at least one hole for a fastener, said base plates being malleable at least in areas thereof adjacent the extension.

From a further aspect, the abutment plates may comprise base plates which are provided with at least two holes for fasteners, a first hole being an elongated hole and a second hole being circular, wherein said holes are arranged on either side of the extension.

From a further aspect, the abutment plates may comprise base plates, said base plates having an anterior end that is pointed. The base plates may have a posterior end that is blunt.

In one embodiment, said base plates have an anterior end that is pointed and wherein said elongated hole is located at the anterior side of the extension.

From another aspect, the abutment plates may have on end that is sharp and triangular in shape so as to dissect automatically between the mucoperiosteum and the bone and another end that is blunt as to prevent damage to palatal blood vessels.

From another aspect, the ends of said distraction module can be provided with a first hole and wherein said extensions are provided with a second hole, said first and second holes being for passage of a connector adapted to connect the distractor module end to the extension. The connector may be a thread or wire or the like.

In addition, the extensions may be box-shaped and may contain slit-like openings (8) to accommodate a wire or suture (10) that passes also through an opening (9) in the disk-shaped end of the arm, allowing for arming the device before osteosynthesis.

From another aspect, the invention provides a distraction apparatus for expansion of an upper jaw bone after osteotomy by application of distraction forces directly to a bone of a palate with the aim to reconstruct the jaw by increasing a distance between two op-posing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, and wherein the abutment plates comprise malleable base plates which are provided with at least one hole for a fastener, said base plates being malleable at least in areas thereof adjacent the extension.

From yet another aspect, the invention provides a distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, wherein said ends of said distraction module are provided with a first hole and wherein said extensions are provided with a second hole, said first and second holes being for passage of a connector adapted to connect the distractor module end to the extension. The connector may be releasable for temporarily use. The connector may be wire- or thread-shaped.

From still another aspect, the invention provides a distraction apparatus for the expansion of an upper jaw bone after osteotomy by application of distraction forces directly to a bone of the palate with the aim to reconstruct the jaw by increasing the distances between two op-posing bone segments by means of gradually stretching, comprising a distraction module having two outer ends located at a mutual distance from each other, wherein said mutual distance can be altered by means of an expansion screw in the distraction module, and two abutment plates that can be fixed directly to a surface of the bone of the palate, said surface facing an oral cavity, wherein said abutment plates are provided with an extension, wherein said extensions have a design that allows fixation of a respective end of the distraction module onto or into the extension of the abutment plates, wherein said ends of said distraction module and said extensions are provided with first and second connecting means hingingly interengaging each other for said fixation, wherein the abutment plates comprise base plates, said base plates having an anterior end that is pointed and/or having a posterior end that is blunt.

In one further embodiment, the abutment plates may comprise base plates which are provided with at least two holes for fasteners, a first hole being an elongated hole and a second hole being circular, wherein said holes are arranged on either side of the extension, wherein said elongated hole is located at the anterior side of the extension.

From another aspect, the invention provides a method for widening an upper jaw bone (maxillae) after osteotomy, using a distraction apparatus comprising two abutment plates and a distraction module, said abutment plates each being provided with a base plate and an extension, said distraction module having two opposite ends, wherein said extensions and said distraction module ends are shaped for interengagement, wherein the distraction apparatus is placed into an oral cavity with the distraction module ends and the extensions interengaging one another and being temporarily secured to one another, wherein the abutment plates are fixed directly to bone of the palate on either side of a split in the bone of the palate by means of said base plates, said extensions piercing through palatal soft tissue into the oral cavity, whereafter the distraction module is expanded to exert a force on the extensions biasing the abutment plates away from one another and the temporarily securement is released.

From another aspect, the invention provides a distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, herein said abutment plates are provided with an extension for extending into the oral cavity, wherein said extensions of the abutment plates are hingedly connected to the respective ends of the distraction module.

In one embodiment, said ends of the distraction module are conical.

The extensions may be provided with a female sleeve in which the conical end of the distraction module fits.

In one embodiment, the ends of the distraction module hingingly abut the extensions of the abutment plates.

From a further aspect, the invention provides a distraction apparatus for the expansion of the upper jaw with application of the forces directly to the palatal bone with the aim to reconstruct the jaw by increasing the distances between the two opposing bone segments by means of gradual stretching characterised in that it has the following parts:
  two abutment plates, that are fixed directly to the palatal shelves and which allow to fit of a disk-shape male wing of a distraction module into hollowed-out shaped female openings in the box-like extensions on their base-plate;
  expansion screws, called distraction modules, of different lengths, with expansion arms provided with in plane, disk-shaped male wings, straight in cross-section.

The invention further provides an embodiment in which the device has following parts:
  distraction modules of increasing lengths, with at both sides extending arms with disk-like wings that fit into the hollowed side walls of the extension boxes on the abutment plates. The disk-like extensions are in the plane of the rods and have a hole to accommodate a wire or suture;
  two abutment plates, that are fixed to the palatal shelves, with a screw into a slotted hole at one side of the extension box and a screw in a round hole at the other end of the box;
  a box-like extension, provided by a slot to fit the male wing of the expansion arms of the distraction module into; the box-like extension has a slit or opening in its upper and/or lower wall, parallel to the base-plate, situated at the level of the hole in the disk-like extension, to accommodate a wire or suture;
  a base-plate that is malleable in the area next to the box-like extension.

The distraction module may comprise a mechanical jack-screw, which comprises three parts which fit into one another, the central segment having the largest diameter, and being provided at its ends with internal turns of opposite direction and different sizes, into which two mutually opposite telescopic arms fit, which are able to move into one another and can move completely into and out of the central connecting sleeve. The telescopic arms may have virtually the same length as the connecting sleeve.

The wings at the ends of the telescopic arms allow the distraction module to be fitted into the extension boxes of the abutment plates. The wings can be shaped in the form of a half or complete disk, in plane with the arms. In cross-section, the disks can be straight. They can have an opening to accommodate a wire or suture that passes also in a slotted hole or opening in the box-like extension of the abutment plate, allowing assembly before fixation on the palatal shelve. The abutment plates can have malleable base-plates with a circular and slotted hole for improved positioning related to the dental roots. The first side walls of the boxlike extension are hollowed in the palatal plane section, as to accommodate part of the circumference of the disk-like extensions of the distractor arms. The second side walls diverging from each other in direction towards the distraction module, so that the opening in the box is depouille in the frontal section, providing a degree of freedom for the wings to be accommodated according to the slope angle of the palatal shelves. The largest width of the wings is smaller than the width of the opening of the boxes, so that the module can be easily placed and removed during (re)placement. Due to the convex shape of the side edges of the wings, the wings engage in the hollowed first side walls of the box. When the distraction module assumes an inclined orientation, the wings will rotate within the boxes and remain therein, in spite of the possible presence of increased forces.

The increased fit of the expansion arms into the box-like extensions allows oblique placement and reducing inadvertent loss of the distraction module. This is in particular advantageous in cleft palate patients.

The male wings of the expansion arms of the distractor modules provide a reduced risk to dislocate from the female slots in the box-like extensions on the abutment plates, that the components can be assembled with a wire or suture before osteosynthesis (hence reducing considerably operating time especially for novice surgeons), that the anterior end of the abutment plates dissects by itself between the mucoperiosteum and the bony surface, that the posterior end of the abutment plates is blunted to prevent damage to the palatal blood vessels, that one of the openings for the osteosynthesis screws is a "long hole", hence allowing positional adjustment related to the dental structures, and that the base plate is made malleable to accommodate surface anatomy and to prevent stripping of the bone thread.

From a further aspect, the invention provides a distraction apparatus for the expansion of the upper jaw with application of the forces directly to the palatal bone with the aim to reconstruct the jaw by increasing the distances between the two opposing bone segments by means of gradual stretching characterised in that it has the following parts:

two abutment plates, that are fixed directly to the palatal bone and of which an extension pierces through the palatal soft tissue into the oral cavity, having a design that allows fixation of the end of a distraction module;

expansion screws, called distraction modules, of different lengths, with bores for blocking screws.

In one embodiment the device has following parts:

two abutment plates, that are fixed to the palatal bone (processus palatinus ossis maxillaris), with screws into drill holes (in one embodiment) or with other means such as pins, left and right under the soft tissues;

a box-like extension provided by a slot (in one embodiment) or other hinge mechanism to fit or fix the distraction module into or onto. The extension pierces the soft tissues;

expandable parts (distraction modules) of different, increasing lengths, in one embodiment four, with at both sides connections possibilities (such as wings) that fit into or onto the extension of the abutment plates.

In one embodiment, the distraction module comprises a telescopic screw, called the distraction module. The telescopic screw allows the distraction section to be kept compact, leading to a greater stretching with a small initial length. Modules of different initial and final lengths allow to choose in the individual case for the proper initial size, and to change for a bigger size when deemed necessary.

The screws used to fix the abutment plate in the palate have appropriate lengths in order to avoid damage to the roots of the teeth.

After a latency period of four to seven days, activation can start, by ⅓ mm daily. After a distraction period of one to two weeks, and a stabilisation period of one to three months, the orthodontist can start with fixed orthodontic appliances. One or two months later, the distractor is removed. Complete bony consolidation occurs in the median vertical distraction area and in the lateral horizontal distraction areas.

The flat conical shaped wing (in one embodiment) at one of the sides of the telescopic arm allows the distraction module to be fitted into the extension box of the abutment plate.

A colour or form code on the connecting sleeve allows to control the speed of the gradual stretching.

Three bores with thread at one side of the connecting sleeve allow to block the movements of the module with a blocking screw.

The apparatus can be made of titanium. This material is well known for its optimum biocompatibility, both for incorporation into the bone (osteointegration) and for incorporation into the soft tissue parts. No allergies to titanium have been described. Dimetalosis has been ruled out. The complete device and the fixation screws may consist of titanium.

An aspect of the invention is the application of the expansion force directly onto the bone, and not indirectly over the teeth.

Assets of this invention compared to tooth-borne appliances (that are patented by Leone, Schellino and Modica (EP 0846446), by Palmisano (WO 9629964), by Bernhard Förster (WO 9628110 and WO 9810708), by Klapper and George (EP 0706349), can be that there is no or less rotation of the jaw segments in the frontal plane by its high level of force application, that it results in orthopaedic and not orthodontic expansion, that dento-alveolar relapse is not to be expected during and after the expansion, that the interchangeable expansion-modules allow to continue expansion without having to resort to the fabrication of a new appliance, and that the orthodontist has all teeth available to start with active orthodontic treatment before the stabilisation period has ended.

These and other features of the invention will emerge from the following description, in which reference is made to the appended drawings, which show an exemplary embodiment of an apparatus according to the invention.

The above-mentioned aspects can be applied separately or in combination.

DETAILED DESCRIPTION OF THE DRAWINGS

In these figures, identical numerals refer to identical or similar elements.

A distraction osteotomy is a surgical operation for correcting deformity or curvature of a bone which is curved or too short, the bone being split into at least two bone segments being joined together again by dynamic osteosynthesis, that is to say gradual repositioning and fixation of the bone segments with the aid of guided rods, small metal plates, screws, pins, bone pegs or hoops.

The distraction apparatus' depicted in the figures serves to widen the upper jaw, after a cortical mono- or bilateral horizontal osteotomy and a vertical median or paramedian osteotomy, or when the patient is young enough, by expanding the median suture without additional corticotomies/osteotomies. In FIGS. 1-6, a first embodiment of the invention is depicted.

Figure 1:
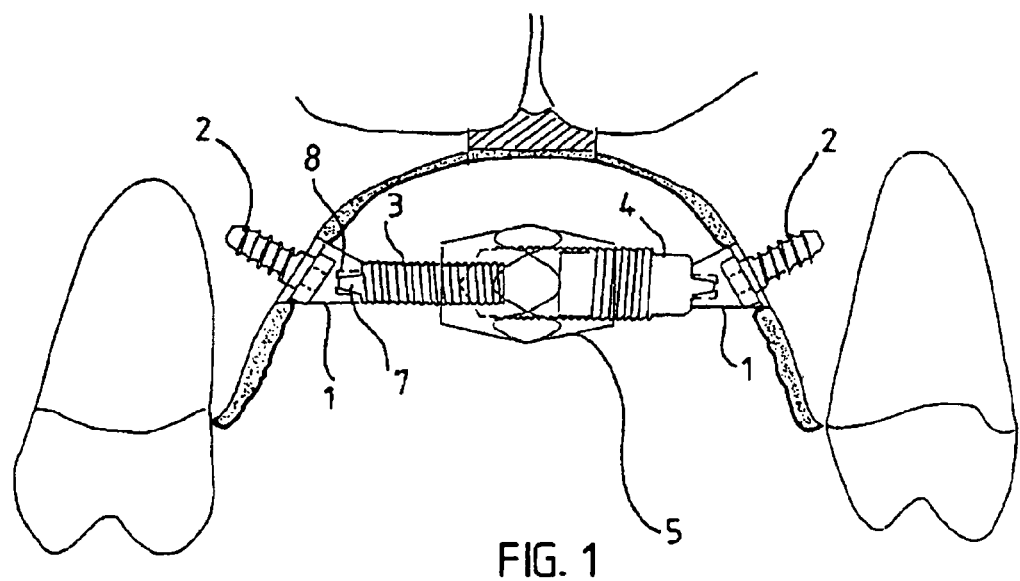
FIG. 1 shows a front view, looking from outside the mouth inwards of a first embodiment of a distraction apparatus in the extended position on the palate according to the invention on a scale of 2:1.
Figure 2:
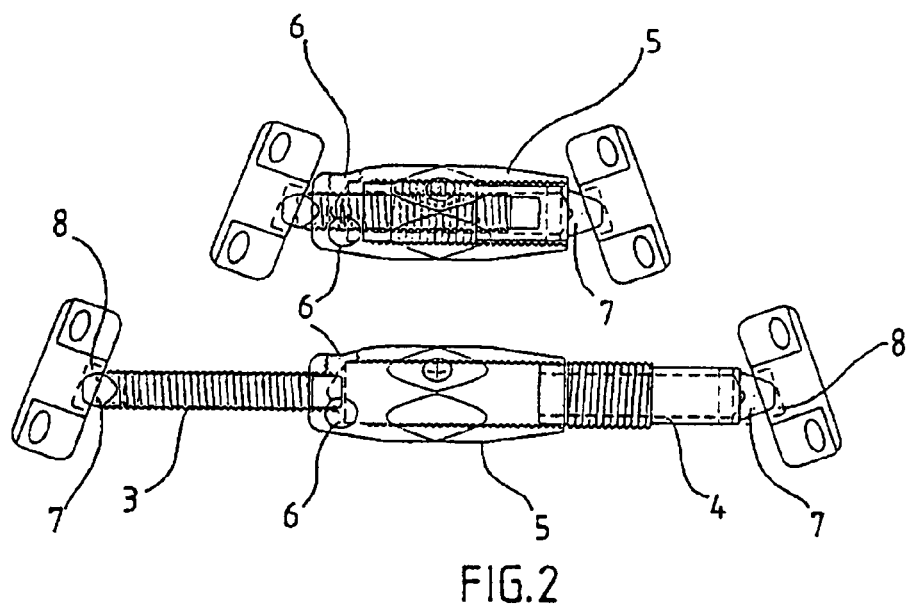
FIG. 2 shows a top view of an apparatus in a contracted and extended position.
Figure 3:
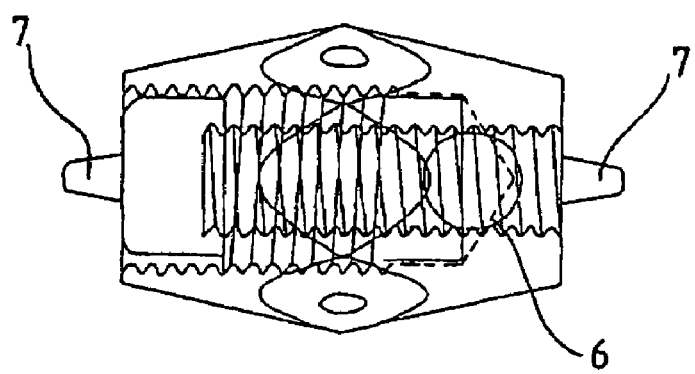
FIG. 3 shows a frontal view of a distraction module in a contracted position on a scale of 4:1.
Figure 4:
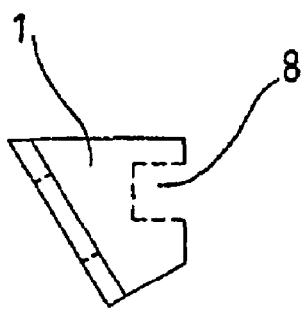
FIG. 4 shows a side view of an abutment plate with box extension on a scale of 4:1.
Figure 5:
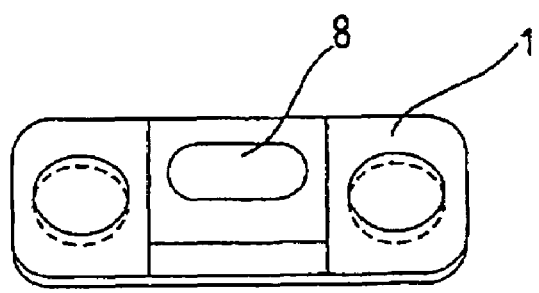
FIG. 5 shows a top view of an abutment plate with an extension on scale 4:1.
Figure 6:
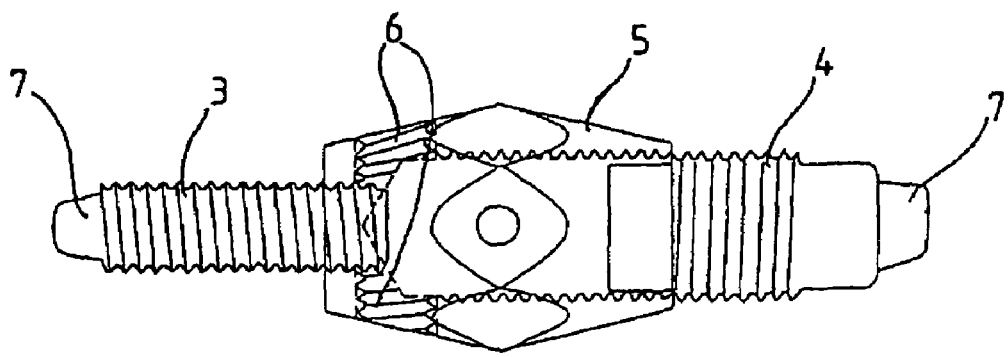
FIG. 6 shows the top view of a distraction module in extended position on a scale of 4:1.

The distraction apparatus depicted in FIG. 1 serves to widen the upper jaw, after a cortical bilateral horizontal osteotomy and a vertical median osteotomy. It comprises the following parts:

two abutment plates 1, fixed with screws or pins on the palatal bone (processus palatinus ossis maxillaris) left and right of the midline;

a distraction module, depicted in FIGS. 3 and 6, in different lengths.

The distraction module is a mechanical jackscrew consisting of three parts which fit into one another. The central one has the largest diameter, in order to act as a connecting sleeve 5 and is provided at its ends with internal threads of opposite direction and different sizes, into which two mutually opposite telescopic arms 3, 4 fit, which are able to move into one another and have virtually the same length as the central connecting sleeve 5, so that they can move completely into and out of the connecting sleeve.

The connecting sleeve 5 has three bores with internal thread 6 to receive a blocking screw.

The free ends of the telescopic arms bear a male conical wing 7, fitting into the female sleeve 8 of the abutment plates 1, in this example.

In FIGS. 7-10, a second embodiment of the invention is depicted.

Figure 7:
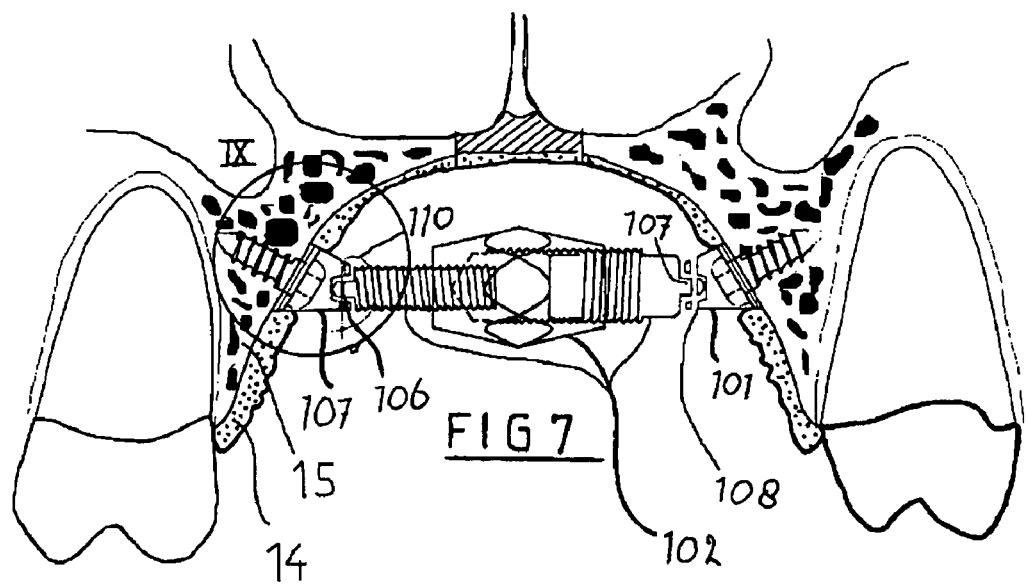
FIG. 7 shows a front view, looking from outside the mouth inwards of a second embodiment of a distraction apparatus in the extended position on the palate according to the invention on a scale of 2:1.
Figure 8:
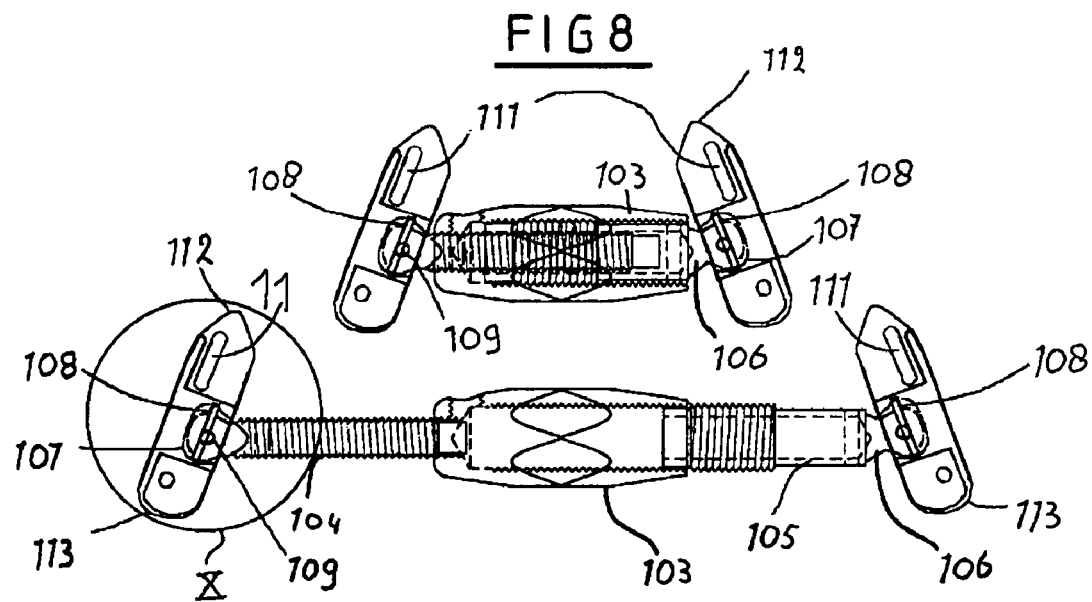
FIG. 8 shows a top view of an apparatus in a contracted and extended position.
Figure 9:
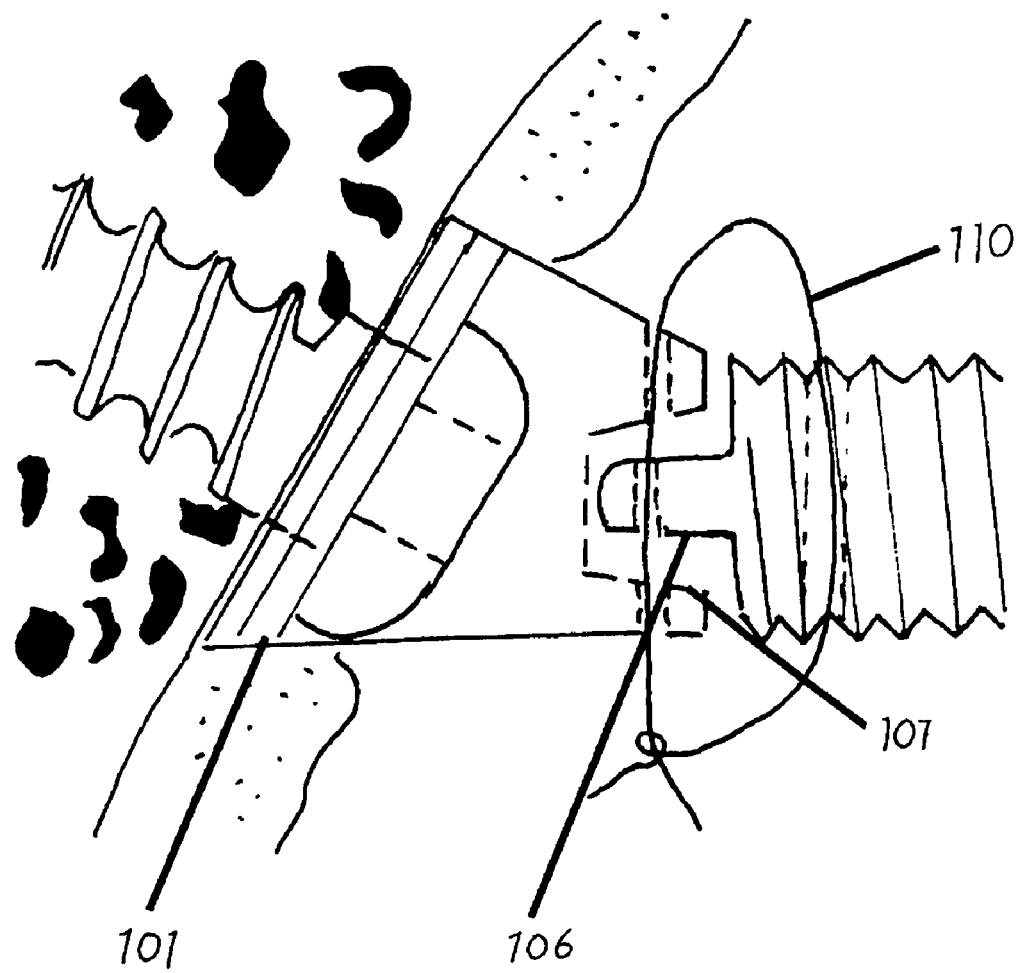
FIGS. 9 and 10 show details of FIGS. 7 and 8, respectively.
Figure 10:
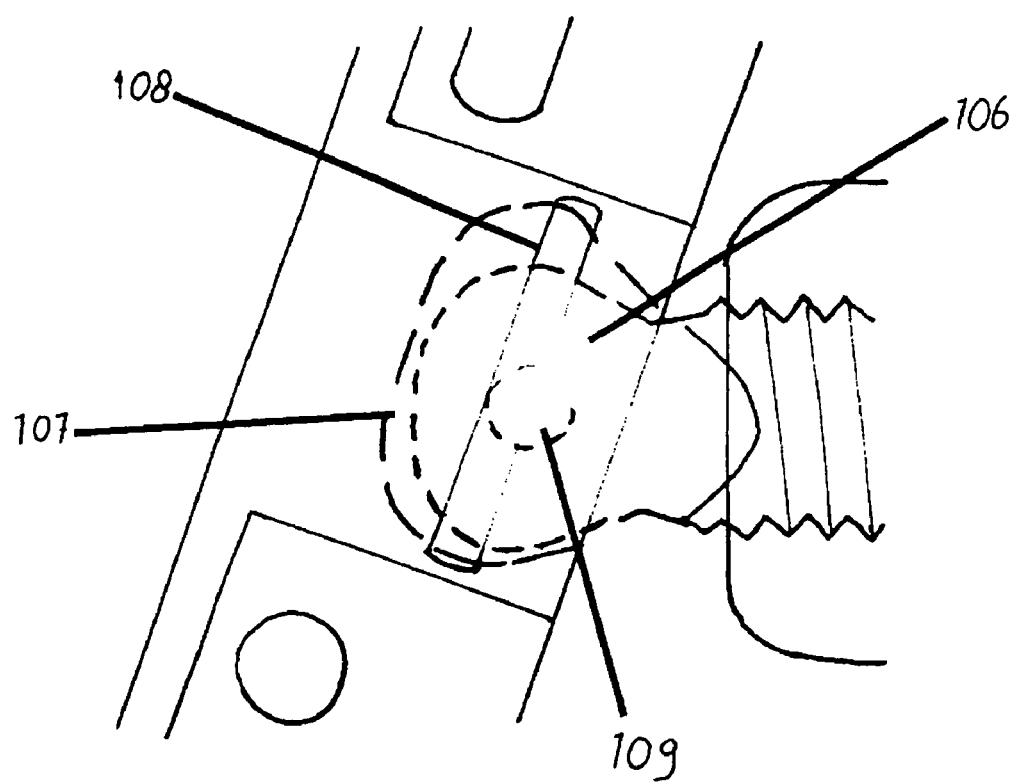

The distraction apparatus of FIG. 7 comprises the following parts:

two abutment plates 101, fixed with screws, tacks or pins on the maxillary palate or the palatal bone, left and right of the midline;

a distraction module 102, in different lengths.

The distraction module is a mechanical jackscrew consisting of three parts which fit into one another. The central one has the largest diameter, in order to act as a connecting sleeve 3 and is provided at its ends with internal threads of opposite direction and different sizes, into which two mutually opposite telescopic arms 104, 105 fit, which are able to move into one another.

The free ends of the telescopic arms bear a male wing 6, fitting into the female sleeve 107 of the abutment plates 101. The male wings 6 have the shape of a disk, circular or semicircular, fitting in the hollowed-out side walls of the sleeve 107 in the box-like extensions on the abutment plates. The curved edge of the disks may extend over more than 180 degrees, for instance over approximately 245 degrees, as depicted. A neck region has been formed at the transition area of the wings to the threaded arm portion.

The box-like extensions are provided with slit-like openings 108 on the caudal and/or cranial side, at the level of an opening 109 in the disk-like extension 106 of the expansion arm 104,105 to accommodate a wire or suture 110, in order to assemble the distractor components into one unit before fixation on the bone. The hollowed side walls of the box-like extensions more or less correspond to the curved edge of the disks and extend to the neck region of the arm ends in the opening area of the box, yet allowing insertion and removal of the disks into and from the box-like extensions, if desired.

The wings of the abutment plate 1 are malleable to accommodate local surface anatomy and to prevent stripping of the bony thread. The wings are provided by at least one slotted hole 111 to accommodate local dental root anatomy;

The abutment plates 102 have at one end a triangularly shaped, self dissecting end 112, which slips between mucoperiosteum 14 and bone 15 as a dissecting instrument. The other end 113 is rounded and blunted to avoid damage to the palatal blood vessels.

The invention claimed is:

1. Distraction apparatus for expansion of an upper jaw bone after osteotomy by application of distraction forces directly to a bone of a palate with the aim to reconstruct the jaw by increasing a distance between two opposing bone segments by means of gradually stretching, comprising:
   (a) a distraction module comprising:
     a connecting sleeve having at opposite ends internal threads of opposite direction;
     two telescopic arms having at proximal ends external threads of opposite direction and corresponding to the internal threads of the connecting sleeve, and each arm having a distal end located at a mutual distance from each other;
     wherein the distal ends of the distraction module arms are disk-shaped and have arched surfaces;
     the telescopic arms being threadedly connected to the connecting sleeve to allow the arms to move distally apart by rotation of the connecting sleeve; and
   (b) two abutment plates that are non-integrally formed with the distraction module and are adapted to be secured to the bone of the palate and having fixation means to directly fix the abutment plates to a surface of the bone of the palate, each abutment plate comprising:
     a bone contacting surface;
     extensions extending away from the bone contacting surface;
     a receiving sleeve formed by the extensions of each abutment plate,
     each receiving sleeve being shaped to rotatably and hingeably receive the disk-shaped distal ends of the distraction module arms;
     wherein the abutment plates are hingeably and releasably connected to the distal ends of the distraction module arms by the arm distal ends fitting into the receiving sleeves of the plates to thereby allow rotational movement between the distraction module and the abutment plates; and
     wherein the distal end of the distraction module arms can be removed from the receiving sleeves of the plates by rotating the connecting sleeve.

2. Distraction apparatus according to claim 1, wherein the distraction module arm ends have a convex disk and edge.

3. Distraction apparatus according to claim 2, wherein the end edge is circular.

4. Distraction apparatus according to claim 1, wherein the distraction module arm ends are widened with respect to an arm portion connection to the ends.

5. Distraction apparatus according to claim 1, wherein the disk-shaped outer ends of the distraction module arms merge into the threaded arm portions of the distraction module via a neck, the necks having a smaller cross-sectional area than the threaded arm portions.

6. Distraction module apparatus according to claim 5, wherein the receiving sleeve further comprises side walls that extend to an area proximate the neck of the distraction module.

7. Distraction apparatus according to claim 1, wherein the disk-shaped ends of the distraction module arms merge into the distraction module arms via a neck, wherein the receiving sleeve has an opening which is narrowed with respect to the receiving sleeve and adapted to accommodate the neck.

8. Distraction apparatus according to claim 1, wherein the abutment plates comprise base plates which are provided with at least one hole for a fastener, said base plates being malleable at least in areas thereof adjacent the extension.

9. Distraction apparatus according to claim 1, wherein the abutment plates comprise base plates which are provided with at least two holes for fasteners, a first hole being an elongated hole and a second hole being circular, wherein said holes are arranged on either side of the extension.

10. Distraction apparatus according to claim 9, wherein said base plates have an anterior end that is pointed and wherein said elongated hole is located at the anterior side of the extension.

11. Distraction apparatus according to claim 1, wherein the abutment plates comprise base plates, said base plates having an anterior end that is pointed.

12. Distraction apparatus according to claim 1, wherein the abutment plates comprise base plates, said base plates having a posterior end that is blunt.

13. Distraction apparatus according to claim 1, wherein the abutment plates have one end that is sharp and triangular in shape so as to dissect automatically between the mucoperiosteum and the bone and another end that is blunt as to prevent damage to palatal blood vessels.

14. Distraction apparatus according to claim 1, wherein said distal ends of said distraction module arms are provided with a first hole and wherein said extensions are provided with a second hole, said first and second holes being aligned for passage of a connector adapted to connect the distraction module arm distal end to the extension.

15. Distraction apparatus according to claim 14, wherein the connector is a thread.

16. Distraction apparatus according to claim 1, wherein the distal ends of the distraction module arms are provided with a hole and wherein the extensions contain slit-like openings designed to be aligned with the arm hole when the device is assembled to accommodate a wire or suture that passes through the hole and the slit-like openings, allowing for arming the device before osteosynthesis.

17. Distraction apparatus according to claim 1, further comprising:
 an opening through each outer end of the arms of the distraction modules;
 slit-like openings through the extensions of each abutment plate, the slit-like openings of each abutment plate aligning with the opening of one of the outer ends of the distraction module;
 a first and second connector, the first connector extending through the slit-like opening of the extension of one of the abutment plates and through the opening in the outer end of one of the arms, and the second connector extending through the slit-like opening of the extension of the other abutment plate and through the opening in the outer end of the other; and
 wherein the connectors allow assembly of the abutment plates to the distraction module before fixation to the bones of the palate.

18. Distraction apparatus according to claim 17, wherein the connectors comprises a wire or a suture for temporary securing of the outer ends of the distraction module to the extensions of the abutment plates.

19. Distraction apparatus for expansion of an upper jaw bone after osteotomy by application of distraction forces directly to a bone of a palate with the aim to reconstruct the jaw by increasing a distance between two opposing bone segments by means of gradually stretching, the distraction apparatus comprising:
 a distraction module having a connecting sleeve having internal threads at opposite ends for receiving two threaded arm portions of arms having external threads and extending in opposite directions, two outer ends at distal ends of the arms and located at a mutual distance from each other, the outer ends having a conical shaped edge, wherein said mutual distance can be altered by means of an expansion screw in the distraction module, and
 two abutment plates that are non-integrally formed with the distraction module and that have a bone contacting surface, and are adapted for being fixed directly to a surface of the bone of the palate, wherein said abutment plates are provided with extensions for extending away from the bone contacting surface, the extensions defining a receiving sleeve designed to rotatably and hingeably receive the conical-shaped end of the distraction module, wherein said extension of the abutment plates are hingedly connected to the respective ends of the distraction module,
 wherein said ends of said distraction module are provided with a first opening and wherein said extensions are provided with a second opening, said first and second openings being for passage of a connector adapted to connect the distraction module end to the extension,
 wherein the conical shaped edge of the outer ends and corresponding shaped edge of the receiving sleeves allow for rotational movement of the abutment plates relative to the distraction module; and
 wherein the distal end of the distraction module arms can be removed from the receiving sleeves of the plates by rotating the connecting sleeve.

20. Distraction apparatus according to claim 19, wherein the abutment plates comprise base plates, said base plates having an anterior end that is pointed.

21. Distraction apparatus according to claim 20, said base plates having a posterior end that is blunt.

22. Distraction apparatus according to claim 20, wherein the base plates comprise at least two holes for fasteners, a first hole being an elongated hole and a second hole being circular, wherein said holes are arranged on either side of the extension, wherein said elongated hole is located at the anterior side of the extension.

23. A method for widening an upper jaw bone after osteotomy, comprising:
 (a) attaching to the upper jaw bone two separate abutment plates, each plate comprising:
  (i) a bone contacting surface;
  (ii) an extension extending away from the bone contacting surface;
  (iii) a receiving sleeve on the extension;
 (b) inserting a distraction module into the receiving sleeves of the two abutment plates, wherein the distraction module comprises:
  (i) a connecting sleeve having at opposite ends internal threads of opposite direction;
  (ii) two telescopic arms having at proximal ends external threads of opposite direction and corresponding to the internal threads of the connecting sleeve, and each arm having a distal end located at a mutual distance from each other, the distal ends of the distraction module arms being conical-shaped;
  (iii) the telescopic arms being threadedly connected to the connecting sleeve;
wherein the conical-shaped distal ends of the arms are inserted into the receiving sleeve on the extension of the abutment plate;
(c) turning the connecting sleeve to thereby telescopically expand the distraction module arms and apply a separating force to the bone;
wherein the distraction module arms are rotatably and hingably connected to the abutment plates; and
wherein the distraction module is disconnected from the abutment plates by rotating the connecting sleeve.

24. A method for widening an upper jaw bone after osteotomy, comprising:
(a) attaching to the upper jaw bone a distraction module assembly comprising:
  (i) two abutment plates, each plate comprising:
    a bone contacting surface;
    an extension extending away from the bone contacting surface;
    a receiving sleeve on the extension having a slit;
  (ii) a distraction module comprising:
    a connecting sleeve having at opposite ends internal threads of opposite direction;
    two telescopic arms having at proximal ends external threads of opposite direction and corresponding to the internal threads of the connecting sleeve, and each arm having a distal end located at a mutual distance from each other, the distal ends of the distraction module arms being conical-shaped and having a hole therein;
    the telescopic arms being threadedly connected to the connecting sleeve;
  wherein the conical-shaped distal ends of the arms are inserted into the receiving sleeve on the extension of the abutment plate; and
  (iii) means for holding the distal ends of the distraction module arms together with the plate receiving sleeves, wherein the means traverses the hole in the module arm and the slit in the respective receiving sleeve;
  wherein the distraction module is attached to the bone by securing the abutment plates to the bone, and subsequently removing the holding means; and
(b) subsequently turning the connecting sleeve to thereby telescopically expand the distraction module arms and apply a separating force to the bone;
wherein each of the distraction module arms are rotatably and hingably connected to the respective abutment plate by having the distraction module arm distal ends housed within the receiving sleeve of the abutment plate; and
wherein the distraction module is disconnected from the abutment plates by rotating the connecting sleeve.

* * * * *

UNITED STATES PATENT AND TRADEMARK OFFICE
CERTIFICATE OF CORRECTION

| | | |
|---|---|---|
| PATENT NO. | : 7,588,579 B2 | Page 1 of 1 |
| APPLICATION NO. | : 11/070862 | |
| DATED | : September 15, 2009 | |
| INVENTOR(S) | : Maurice Yves Mommaerts | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this

Twenty-first Day of September, 2010

David J. Kappos
*Director of the United States Patent and Trademark Office*